United States Patent
Göbel et al.

(10) Patent No.: US 9,627,105 B2
(45) Date of Patent: Apr. 18, 2017

(54) COAXIAL CABLE FOR THE ELECTRICAL TRANSMISSION OF A RADIOFREQUENCY AND/OR HIGH-SPEED DATA SIGNAL, ROTATING JOINT COMPRISING TWO SUCH COAXIAL CABLES, AND RETAINING APPARATUS COMPRISING AT LEAST ONE SUCH ROTATING JOINT

(71) Applicant: Ondal Medical Systems GmbH, Hünfeld (DE)

(72) Inventors: Andreas Göbel, Eiterfeld (DE); Fritz Ickler, Kirchheim (DE)

(73) Assignee: Ondal Medical Systems GmbH, Hünfeld (DE)

( * ) Notice: Subject to any disclaimer, the term of this patent is extended or adjusted under 35 U.S.C. 154(b) by 0 days.

(21) Appl. No.: 14/440,039

(22) PCT Filed: Nov. 7, 2013

(86) PCT No.: PCT/EP2013/003354
§ 371 (c)(1),
(2) Date: Apr. 30, 2015

(87) PCT Pub. No.: WO2014/075780
PCT Pub. Date: May 22, 2014

(65) Prior Publication Data
US 2015/0294767 A1    Oct. 15, 2015

(30) Foreign Application Priority Data
Nov. 13, 2012 (DE) .................. 20 2012 010 854 U

(51) Int. Cl.
*H02G 3/02* (2006.01)
*H01B 11/18* (2006.01)
(Continued)

(52) U.S. Cl.
CPC .......... *H01B 11/1895* (2013.01); *A61B 90/50* (2016.02); *F16M 11/08* (2013.01);
(Continued)

(58) Field of Classification Search
CPC .............. H01B 11/1895; H01B 7/1875; H01B 11/1808; H01B 11/00; H01B 11/02;
(Continued)

(56) References Cited

U.S. PATENT DOCUMENTS 3,963,854 A * 6/1976 Fowler ............... H01B 11/1808
174/107
6,417,454 B1 * 7/2002 Biebuyck ........... H01B 11/1826
174/106 R
(Continued)

FOREIGN PATENT DOCUMENTS

CN         2563711 Y      7/2003
CN       201226265 Y      4/2009
(Continued)

*Primary Examiner* — Angel R Estrada
(74) *Attorney, Agent, or Firm* — Seed Intellectual Property Law Group LLP

(57) ABSTRACT

The invention relates to a coaxial cable for electrical transmission of a high-frequency and/or high-speed data signal, in particular for medical-engineering applications, comprising a arranged radially inside and a plurality of shields which surround the core radially outside, the core exhibiting a litz with a plurality of individual wires. The invention further relates to a rotary coupling with two coaxial cables of such a type, and also to a holding device, in particular a ceiling support, with such a rotary coupling.

9 Claims, 2 Drawing Sheets

Figure 1:
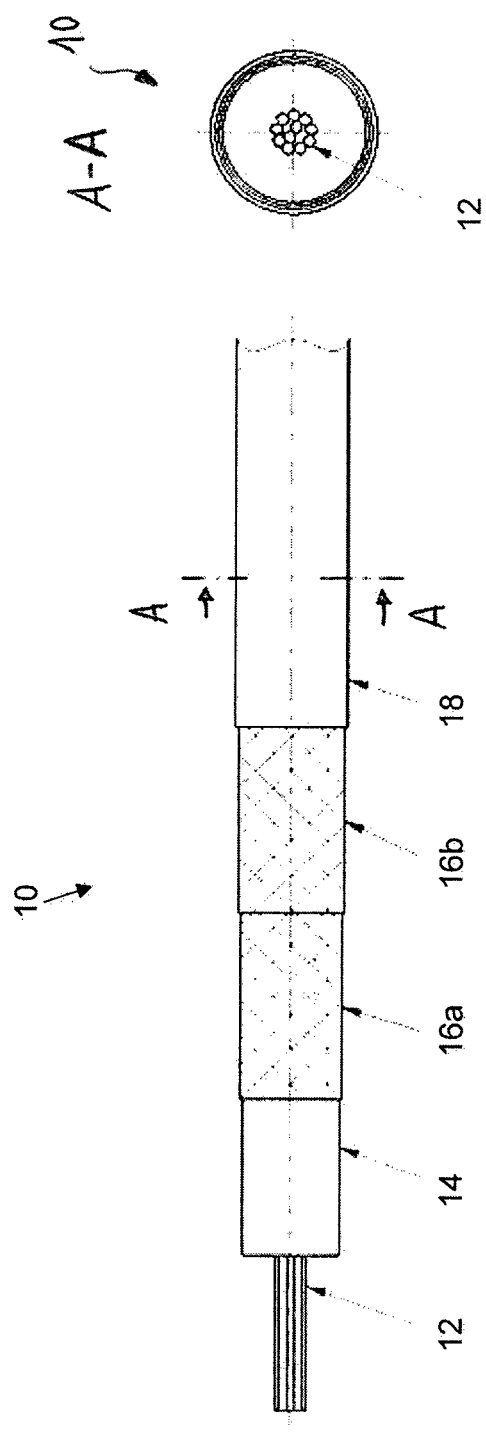

(51) Int. Cl.
*F16M 11/08* (2006.01)
*F16M 11/20* (2006.01)
*F16M 13/02* (2006.01)
*H01B 7/18* (2006.01)
*H01R 4/20* (2006.01)
*H02G 7/00* (2006.01)
*A61B 90/50* (2016.01)
*H01R 24/40* (2011.01)
*H01R 39/64* (2006.01)

(52) U.S. Cl.
CPC ..... *F16M 11/2014* (2013.01); *F16M 11/2021* (2013.01); *F16M 13/027* (2013.01); *H01B 7/1875* (2013.01); *H01B 11/1808* (2013.01); *H01R 4/20* (2013.01); *H02G 7/00* (2013.01); *F16M 2200/065* (2013.01); *H01R 24/40* (2013.01); *H01R 39/64* (2013.01)

(58) Field of Classification Search
CPC . H01B 11/18; H01B 11/1817; H01B 11/1826; H01B 11/20; H01R 4/20; H01R 4/00; H01R 24/40; H01R 39/64; H02G 7/00; H02G 7/02; H02G 11/00; H02G 15/00; H02G 15/007; F16M 11/08; F16M 11/2021; F16M 13/027; F16M 2200/065; F16M 11/2014; G01R 31/021
USPC ...... 174/68.1, 70 R, 71 R, 72 A, 71 C, 75 C, 174/88 C, 28, 102 R, 106 R, 108, 109, 174/113 R, 120 R
See application file for complete search history.

(56) References Cited

U.S. PATENT DOCUMENTS

| | | | | |
|---|---|---|---|---|
| 7,449,631 | B2* | 11/2008 | Lee | H01B 11/1817 174/28 |
| 7,459,627 | B2* | 12/2008 | Lee | H01B 11/1817 174/28 |
| 7,491,883 | B2* | 2/2009 | Lee | H01B 11/1808 174/28 |
| 7,781,677 | B2* | 8/2010 | Matsubara | H04B 3/30 174/113 R |
| 8,143,517 | B2* | 3/2012 | Detian | H01B 11/20 174/28 |
| 8,147,273 | B2* | 4/2012 | Rabbe | H01R 13/645 439/607.06 |
| 8,796,547 | B2* | 8/2014 | Kukowski | G01R 31/021 174/28 |
| 8,926,336 | B2* | 1/2015 | Gobel | H01R 24/40 439/578 |
| 9,245,668 | B1* | 1/2016 | Vo | H01B 11/02 |
| 9,443,646 | B2* | 9/2016 | Armbrecht | H01B 11/20 |
| 2004/0251390 | A1 | 12/2004 | Wachob | |

FOREIGN PATENT DOCUMENTS

| | | |
|---|---|---|
| EP | 0 170 159 A2 | 2/1986 |
| EP | 2 309 608 A1 | 4/2011 |
| WO | 2011/151081 A1 | 12/2011 |

* cited by examiner

COAXIAL CABLE FOR THE ELECTRICAL TRANSMISSION OF A RADIOFREQUENCY AND/OR HIGH-SPEED DATA SIGNAL, ROTATING JOINT COMPRISING TWO SUCH COAXIAL CABLES, AND RETAINING APPARATUS COMPRISING AT LEAST ONE SUCH ROTATING JOINT

The present invention relates to a coaxial cable for electrical transmission of a high-frequency and/or high-speed data signal, in particular for industrial and medical-engineering applications. The invention further relates also to a rotary coupling with two coaxial cables of such a type, and also to a holding device with at least one such rotary coupling.

In the medical-engineering field it is often necessary to transmit high-frequency and/or high-speed data signals from one device to another. Such devices may be, for example, a computing unit, for instance a computer; a sensor, for example for detecting cardiovascular parameters of a patient; a camera of any type, for example for live transmission of surgeries; devices pertaining to imaging processes, for example X-ray devices, CT scanners, MRT devices or ultrasound devices; or a display unit, for example a monitor.

In connection with the present invention, by the designation "high-frequency data signals" generally radio-frequency signals are understood, but in particular radio-frequency signals having frequencies within the UHF range or above it, i.e. electromagnetic signals having a frequency of about 300 MHz and higher (the UHF bandwidth extends as far as about 3 GHz). Preferably, "high-frequency data signals" also encompass radio-frequency signals having frequencies within the SHF range, i.e. up to about 30 GHz, and, particularly preferably, even radio-frequency signals having frequencies within the EHF range, i.e. up to about 300 GHz. Furthermore, the designation "high-speed data signals" relates to digital data-transmission rates of about 100 kbit/s or more, preferentially transmission rates of about 100 Mbit/s or more, particularly preferably transmission rates of about 100 Gbit/s and even above that. In this way, the coaxial cable is suitable to transmit, for example, images of very high quality via UHF, digital video and/or digital HDTV signals.

The transmission of high-frequency and/or high-speed data signals is particularly prone to interference. Particularly in the medical-engineering field, however, it is frequently absolutely essential that data be transmitted in a manner free from interference. Otherwise there is a risk of serious complications, for example if measurement data and/or control data pertaining to life-sustaining equipment are transmitted in faulty manner. For this reason, a simple shielding of the core of the coaxial cable generally does not suffice for use in the medical-engineering field. Instead of this, several shields are needed, in order to sufficiently protect the data stream in the core of the coaxial cable from external electromagnetic influences that may result in a disturbance of the data-signal transmission. Coaxial cables that exhibit a plurality of shields are already commercially available from some suppliers. A feature that is common to these known coaxial cables is that they have been provided with a massive core.

In operating theatres or in hospital rooms it is frequently an advantage to support a medical-engineering apparatus in movable manner on a holding device, for example on a ceiling support, in order to be able to transfer as needed a medical-engineering device fastened to the holding device into a suitable position relative to a patient and/or to another person, for example the treating physician. In this case a computer connected to the device may have been arranged to one side of the holding device and may have been connected to the device via an appropriate coaxial cable, in particular in order to exchange high-frequency and/or high-speed data signals with the device. A spatial displacement of the device, however, frequently has the result that the coaxial cable deforms albeit, quite possibly, only slightly. The same is true if the apparatus has been attached at the end of a spring arm that has a certain intrinsic elasticity. If the coaxial cable runs in or along the spring arm, the coaxial cable is subject to deformations that have been caused by vibrations of the spring arm.

It has now been observed that, particularly in the event of repeated displacement of a medical-engineering device fastened to a previously described holding device, a commercially available coaxial cable with multiple shielding and massive core, attached to a jib or spring arm of the holding device, fatigues or wears out at the core with time in such a manner that disturbances arise in the course of the transmission of high-frequency and/or high-speed data signals.

It is therefore an object of the present invention to solve the aforementioned problem and to ensure the interference-free transmission of high-frequency and/or high-speed data signals in the medical-engineering field reliably and as durably as possible. In particular, an appropriate transmission of data from or to a device that is movably supported at a holding device is to be reliably ensured.

This object is achieved by means of the features of the independent claim 1. Advantageous further developments are the subject-matter of the dependent claims.

According to a first aspect of the present invention, the object is achieved by means of a coaxial cable for electrical transmission of a high-frequency and/or high-speed data signal, in particular for medical-engineering applications, comprising a core arranged radially inside and a plurality of shields which surround the core radially outside, the core exhibiting a litz with a plurality of individual wires.

Inasmuch as the core exhibits a litz with a plurality of individual wires, it can be bent markedly more easily than a massive core. The coaxial cable according to the invention consequently becomes more flexible overall, and even in the event of repeated deformations is not subjected to any appreciable fatigue phenomena or wear phenomena. Through the combination, according to the invention, of the multiple shielding and the substantially fatigue-free and wear-free core, an interference-free transmission of high-frequency and/or high-speed data signals can be durably ensured.

As is known from the commercially available coaxial cables with multiple shielding, the screens preferentially have differing inside diameters, said shields preferentially surrounding the core concentrically. Furthermore, between the core and the shields at least one dielectric is preferentially provided, and/or the shields are jacketed radially outside by an insulating layer or an insulation.

If the holding device for medical-engineering instruments exhibits a hinge point that permits a swiveling or rotating of portions of the holding device within a not inconsiderable angular range, for example by more than 20°, then it is advantageous if the coaxial cable exhibits, at at least one of its two longitudinal ends, a first plug member which is adapted to ensure an uninterrupted electrical connection to a second plug member of complementary design, in particular during a relative rotation of the two plug members about their respective axes of longitudinal extent. It is consequently possible to integrate an electrical rotary coupling within the hinge point of the holding device by means of two appropriate coaxial cables, so that the individual coaxial cables are barely deformed or not deformed at all by a swiveling or rotating of the holding device about its hinge point. In this way, the wear of the coaxial cables can be reduced further, and an interference-free signal transmission can be ensured.

By the term "plug member", according to the present invention both a male plug member, i.e. the actual plug, and alternatively also the female counterpart, i.e. the socket matching the plug, are to be understood.

The provision of a previously described plug member is particularly advantageous if the relative rotation amounts to at least 90°, preferentially at least 180°, particularly preferably at least 360°. The greater the angular range, the more freely may the medical-engineering device be placed in space.

In the event of a relative twisting of the two plug members, however, friction occurs between them, which in consequence again results in a wear of material, and consequently in a possible interference occurring in the course of the transmission of data. It is therefore preferred that the plug member exhibits a coating, which is electrically conducting and increases the wear resistance of the plug member. In particular, in this case at least those surface regions of the plug member should be coated appropriately that come into direct contact with surface regions of the plug member of complementary design in the event of the connection, as intended, of the two plug members.

According to a further aspect, the invention relates to an electrical rotary coupling comprising two coaxial cables according to the invention, a first of the two coaxial cables exhibiting a first plug member, and a second of the two coaxial cables exhibiting a second plug member which is designed to be complementary to the first plug member, the first and the second plug members being electrically conducting and being connected to one another so as to be capable of twisting relative to one another. By means of such an electrical rotary coupling, it is possible to largely avoid deformations of the individual coaxial cables, and consequently to reduce the wear, which in turn permits a durably interference-free signal-transmission.

According to a yet further aspect, the invention relates to a holding device for medical-engineering devices, comprising at least one spring arm or jib that is supported so as to be capable of rotating or swiveling about a hinge point, the spring arm or jib exhibiting a previously described rotary coupling in the hinge point. The holding device preferentially takes the form of a ceiling support, so that the floor of the operating theatre or of the hospital room can be kept clear and consequently, for example, can be cleaned better.

Figure 2:
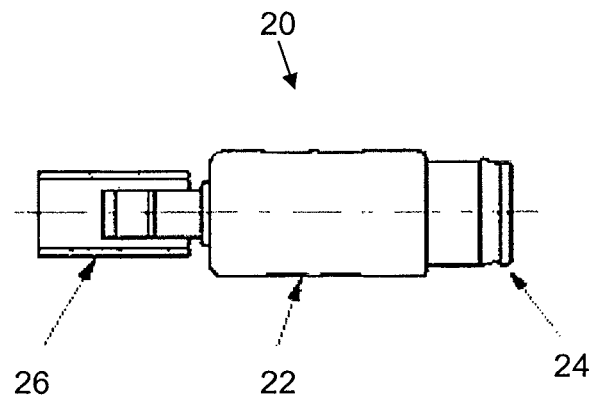
Figure 3:
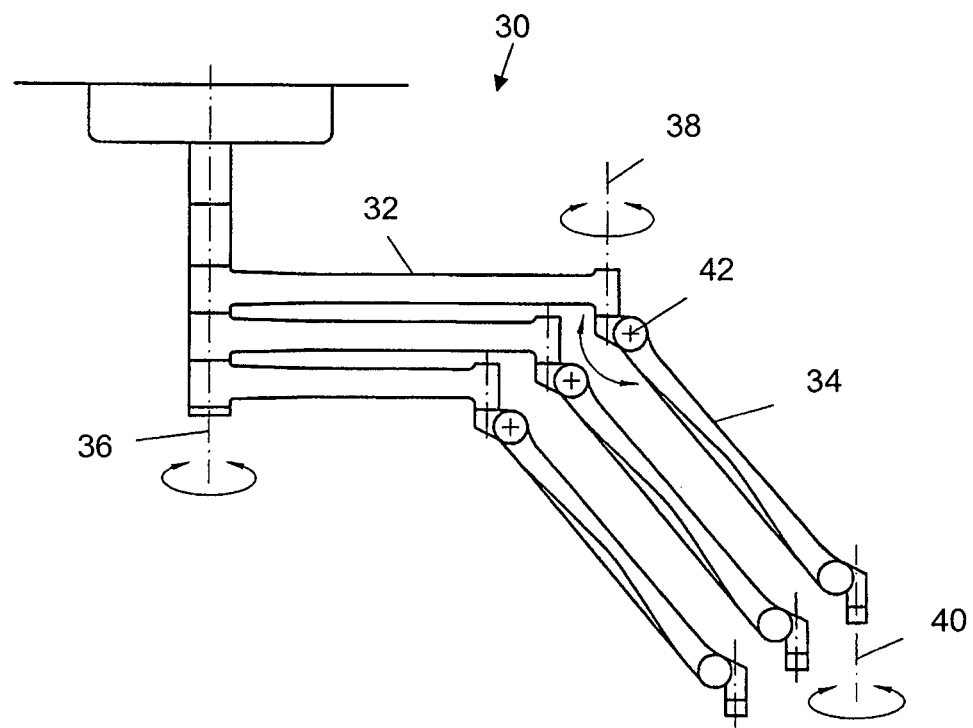

The invention will be elucidated in more detail below in exemplary manner with reference to the Figures. Represented are:

FIG. 1 a side view and a cross-sectional view of a coaxial cable according to the invention, FIG. 2 a plug member for the coaxial cable represented in FIG. 1, and FIG. 3 a ceiling support for medical-engineering devices, comprising several coaxial cables according to the invention.

On the left in FIG. 1 a side view of a coaxial cable 10 according to the invention is represented, wherein, for the purpose of better illustration of its structure, individual layers of the coaxial cable 10 are progressively exposed. On the right in FIG. 1 a cross-sectional view of the coaxial cable 10 corresponding to the indicated section A-A can be seen. The coaxial cable 10 exhibits a substantially concentric structure around its central axis. In the centre of this structure there is located a core 12 which exhibits a litz with a plurality of individual wires. By this means, the coaxial cable according to the invention is particularly pliable or flexible and in the event of deformations is barely subjected to wear phenomena or fatigue phenomena. The core 12 has been surrounded radially on the outside by a dielectric 14. The latter has in turn been surrounded radially on the outside by two shields 16a and 16b. The shields may optionally be formed, for example, from a foil or from a wire mesh. The twofold shielding enables a reliable electrical transmission of a high-frequency and/or high-speed data signal, and hence the use of such coaxial cables for the transmission of sensitive signals in the medical field. Let it be noted that also more than two shields might be provided, in order to achieve a still better shielding. This is advantageous, for example, when the coaxial cable is to be used in the vicinity of strong magnetic fields, for example in the vicinity of an MRT. As a radially outermost layer, the coaxial cable 10 exhibits an insulation 18.

FIG. 2 shows a plug member 20 which is designed to be permanently connected by crimping to a longitudinal end of the coaxial cable 10 represented in FIG. 1. The plug member 20 represented in FIG. 2 is a male plug member (the socket of complementary design is not represented here). The plug member 20 includes a main body 22 with a connecting portion 24, the external surface of which comes into direct contact with surface portions of the socket in the event of a connection, as intended, of the plug member 20 to a socket of complementary design in order to transmit the electrical signals. The plug member 20 is designed to be substantially rotationally symmetrical with respect to its axis of longitudinal extent. A rotation of the plug member 20 relative to the socket of complementary design is consequently possible in the event of a connection, as intended, of plug member 20 and socket, without the signal transmission being interrupted.

The respective contact faces, with which the plug member 20 comes into direct contact with the counter-plug member of complementary design in the event of use as intended, are, in that case, coated, in order to improve the electrical conductivity and/or the wear properties of the plug members.

At the longitudinal end of the plug member 20 opposite the connecting portion 24 said end exhibits an extension which is intended to receive within itself a stripped short end portion of the core of the coaxial cable (not represented). In order to connect the coaxial cable durably to the plug member in such a manner that the two form a unit, a crimp sleeve 26 is provided. When the stripped end portion of the core of the coaxial cable is introduced into the extension of the plug member 20, said crimp sleeve can be plastically deformed by pliers in such a manner that a connection between the coaxial cable and the plug member 20 arises that is no longer separable.

FIG. 3 shows a ceiling support 30 for medical-engineering devices, which exhibits three substantially identically designed jibs. Each jib comprises a first jib portion 32 and a second jib portion 34, the second jib portion 34 taking the form of a to a limited extent, elastic spring arm. At the free longitudinal end of each jib there is located a coupling-point for attaching a medical-engineering device (not represented here), for example a monitor. Each jib exhibits several rotary hinge points, namely rotary hinge points arranged about the axes of rotation 36, 38, 40 and 42, so that a medical-engineering device fastened to the jib may be displaced relatively freely in space.

Within each jib at least one coaxial cable according to the invention (as shown in FIG. 1) is arranged, in order to connect a medical-engineering device fastened to the jib to, for example, a computer placed aside from the ceiling support 30. In the event of a movement of a jib in space, or by virtue of vibrations acting on the elastic spring arm 34, the coaxial cable is repeatedly subject to deformations. At the hinge points at which the deformations of the coaxial cable are particularly pronounced in the event of rotation about the hinge point, for example at the rotary hinge points about the vertical axes 36, 38 and 40, it is advantageous to provide an electrical rotary coupling within the hinge point. For example, a first coaxial cable (as shown in FIG. 1) in the first jib portion 32 might be displaced along the direction of longitudinal extent thereof whereas a second coaxial cable in the second jib portion 34 might be displaced along the direction of longitudinal extent thereof. At the rotary hinge point about the axis 38 a first plug member of the first coaxial cable might be in engagement with a second plug member, of complementary design, of the second coaxial cable, in order to that way form an electrical rotary coupling.

Through the use of coaxial cables according to the invention in the jib arms of the ceiling support 30 and as needed through the formation of electrical rotary couplings at the hinge points of the jib arms, a durably interference-free transmission of high-frequency and/or high-speed data signals from or to medical-engineering devices is ensured.

The invention claimed is:

1. A coaxial cable for electrical transmission of a high-frequency and/or high-speed data signal, in particular for medical-engineering applications, comprising a core arranged radially inside and a plurality of shields which surround the core radially outside,
wherein the core exhibits a litz with a plurality of individual wires, wherein the shields have differing inner diameters and surround the core concentrically, wherein exactly two shields are provided that lie against each other in a radial direction.

2. The coaxial cable according to claim 1, wherein at least one dielectric is provided between the core and the shields.

3. The coaxial cable according to claim 1, wherein the shields are jacketed radially outside by an insulating layer.

4. The coaxial cable according to claim 1, wherein the coaxial cable exhibits, at least one of its two longitudinal ends, a first plug member which is adapted to ensure an uninterrupted electrical connection to a second plug member of complementary design, in particular during a relative rotation of the two plug members about their respective axes of longitudinal extent.

5. The coaxial cable according to claim 4, wherein the relative rotation amounts to at least 90°, preferentially at least 180°, particularly preferably at least 360°.

6. The coaxial cable according to claim 4, wherein the plug member (20) exhibits an electrically conducting, the wear resistance increasing coating of the plug member.

7. The coaxial cable according to claim 4, wherein the plug member is substantially rotationally symmetrical and is formed by a main body with a connecting portion and by an extension, provided on the longitudinal end of the plug member opposite the connecting portion, with a crimp sleeve.

8. An electrical rotary coupling comprising two coaxial cables according to claim 1, a first of the two coaxial cables exhibiting a first plug member, and a second of the two coaxial cables exhibiting a second plug member, which is complementary to the first plug member, the first and the second plug members being connected to one another electrically conducting and capable of twisting relative to one another.

9. A holding device, in particular ceiling support, for medical-engineering instruments, comprising at least one spring arm or jib that is supported so as to be capable of rotating or swivelling about a hinge point, the spring arm or jib in the hinge point exhibiting an electrical rotary coupling according to claim 8.

* * * * *